US 6,200,327 B1

(12) United States Patent
Assal

(10) Patent No.: US 6,200,327 B1
(45) Date of Patent: Mar. 13, 2001

(54) DEVICE FOR REPAIRING RUPTURED ACHILLES TENDON

(76) Inventor: Mathieu Assal, 6, avenue de la Grenade, CH-1207, Geneva (CH)

(*) Notice: Subject to any disclaimer, the term of this patent is extended or adjusted under 35 U.S.C. 154(b) by 0 days.

(21) Appl. No.: 09/355,764
(22) PCT Filed: Jan. 30, 1998
(86) PCT No.: PCT/IB98/00121
§ 371 Date: Oct. 21, 1999
§ 102(e) Date: Oct. 21, 1999
(87) PCT Pub. No.: WO98/34566
PCT Pub. Date: Aug. 13, 1998

(30) Foreign Application Priority Data

Feb. 5, 1997 (CH) ........................................ 246/97

(51) Int. Cl.$^7$ .................................................. A61B 17/04
(52) U.S. Cl. ............................................................ 606/148
(58) Field of Search .................................. 606/148, 102, 606/144; 600/587; 33/465, 512, 555.2

(56) References Cited

U.S. PATENT DOCUMENTS 4,723,548  2/1988  Lalonde .
5,251,642 * 10/1993  Handlos ........................... 606/148

OTHER PUBLICATIONS

Derwent Abstract, Soviet Inventions Illustrated, Section PQ, Week 8629, Aug. 1, 1986 and SU 1 169 626 (Danilov), Jul. 30, 1985.
Journal of Bone and Joint Surgery, Vol. 3 77–B, No. 1, Jan., 1995, "A Combined Open and Percutaneous Technique for Repair of Tendo Achillis, Comparison with Open Repair", Masaaki Kakiuchi, Osaka, Japan.

* cited by examiner

Primary Examiner—Michael Buiz
Assistant Examiner—Tan-Uyen T. Ho
(74) Attorney, Agent, or Firm—Pillsbury Madison & Sutro LLP

(57) ABSTRACT

The apparatus for taking hold of a tendon comprises an instrument and a needle. The instrument (20) has a pair of inner prongs (34, 36) designed to be inserted in the peritendinous sheath on either side of the tendon. The instrument also has an outer handle in the form of two outer prongs (33, 37) situated on either side of the inner pair of prongs and in the same plane. These prongs all have orifices on common alignments passing through the tendon. The eye (12) of the needle is of reduced thickness.

15 Claims, 2 Drawing Sheets

DEVICE FOR REPAIRING RUPTURED ACHILLES TENDON

The present invention relates to apparatus used during a surgical operation to repair a broken Achilles tendon, to take hold of the end of the tendon that is attached to the triceps muscle and that is situated within its peritendinous sheath. The apparatus can also be used to take hold of other tendons in the human body.

The Achilles tendon can break following accidental injury or degeneration due to age. The tendon usually breaks transversely about 4 cm above its insertion on the calcaneum, and by contraction of the triceps it rises to a greater or lesser extent inside its peritendinous sheath.

The surgical operation of repairing the tendon consists in taking hold of the top end of the tendon to pull it down so as to bring it end to end with the bottom end which is attached to the calcaneum, and then to suture them together. This operation must therefore restore the original length of the tendon, must minimize adhesion between the tendon and the tissue surrounding it, and must leave as small a scar as possible.

Various techniques are used for taking hold of the tendon, which techniques are more or less invasive, depending on the hospital concerned. One invasive technique consists in making an incision that is long, about 15 cm long, through the posterior cutaneous zone of the leg along the triceps muscle and then along the tendon to the calcaneum in order to find the two ends of the tendon and bring them together. Nevertheless, that technique is disadvantageous because of the great length of the incision through cutaneous tissue and through the peritendon, which serves to vascularize the tendon itself. In addition, this zone has vascularization which is critical and which is highly stressed by rubbing against the heels of shoes.

A technique that is less invasive is described in the article "A combined open and percutaneous technique for repair of tendo achillis" published in January 1995 in "The Journal of Bone and Joint Surgery". In that technique, a small incision, that is 2 cm to 3 cm long, is initially made at the end of the piece of tendon which is attached to the calcaneum. Thereafter, two relatively rigid bent rods are inserted into the peritendinous sheath to place the loop-forming ends thereof on either side of the end of the tendon that is attached to the triceps. A long needle with a thread is then passed respectively through the adjacent skin, the loop of the first rod, the tendon, the loop of the second rod and then out through the skin on the opposite side. Once the thread is in place, the rods are removed, thereby bringing with them the ends of the thread that is engaged in the tendon out through the incision. This procedure is repeated one or two times at different locations on the tendon. It is then possible to pull uniformly on three threads so as to bring the top end of the tendon easily into place and suture it to the bottom end. If so desired, the traction threads can themselves be connected laterally to other threads engaged correspondingly in the bottom end of the tendon.

Nevertheless, the major difficulty of that technique lies in the fact that it is difficult to find the orifice in the top loop of one and then the other bent rod when they are under the skin and when it is desired to insert the needle therethrough.

When working blindly in that way, steps are made to recognize the respective positions of the loops by touch, but that is lengthy and difficult. In addition, in the end, it is never certain whether the needle has indeed passed through the loops until the rods have been pulled back out from the sheath. The operation can then take a long time since it is usually necessary to implant at least six threads. This is prejudicial because it prolongs the duration of anesthesia.

The object of the present invention is to provide apparatus comprising an instrument and an associated needle that considerably facilitate the surgical operation of repairing a tendon, in particular the Achilles tendon by the above-described subcutaneous technique that is not very invasive. As much as possible, the apparatus should avoid any risk of additional injury, should be relatively simple in design so as to be easy to implement, and should be inexpensive to make. The apparatus should also make it possible significantly to reduce the mean length of time required to perform such an operation, while nevertheless making it possible to suture the tendon properly after it has been used.

These objects are achieved by apparatus comprising both an instrument itself comprising a pair of inner prongs designed to be inserted in the sheath on either side of the tendon, and an external handle including an element situated in the same plane as the pair of inner prongs and in register therewith, the element and the pair of inner prongs each presenting at least one respective orifice on a common alignment passing through the tendon; and a needle suitable for being inserted in the orifice of the element to be guided so as to pass through the orifices of the inner prongs.

Thus, after the pair of inner prongs have been inserted in the peritendinous sheath and after the prongs have been positioned on either side of the tendon, which is easily confirmed by touch, the orifice of the handle element makes it possible to guide the needle in a precise direction enabling it to pass without fail, and even though it cannot be seen, through the tendon which, in addition, is held by the prongs while it is being pierced. The operation of threading a thread through the tendon thus becomes particularly rapid, thereby reducing he duration of the surgical operation.

Preferably, the handle element and the pair of inner prongs respectively present the same arrays of orifices in alignment, with the mouths of the orifices in the prongs being chamfered, if so desired.

This characteristic makes it possible advantageously to increase the chances of success in passing the needle rapidly through the tendon, even when the pair of limbs is not exactly in alignment with the tendon. In addition, the array of orifices makes it possible to pass a plurality of threads through before withdrawing the instrument. The chamfered mouths of the orifices make it easy to accommodate small deflections of the needle away from the alignment of the orifices.

Preferably, the two inner prongs form between them an angle lying in the range 2° to 8°, and preferably equal to 4°, the angle being open in the insertion direction. This characteristic enables the pair of prongs to fit closely around the conical outline of the end of the tendon without running the risk of pushing it back further along the sheath.

Preferably, the inner prongs of the instrument are of rectangular cross-section that is flattened with rounded corners, or of flattened oval section, and if so desired the long side of the section tapers towards the end. The internal prongs thus slide better between the tendon and its peritendinous sheath while the instrument is being put into place.

Preferably, the spacing between the two inner prongs is adjustable. The instrument can then be adapted to the various morphologies of patients.

Advantageously, the handle element comprises two outer prongs respectively situated on either side of the pair of inner prongs and lying in the same plane. The instrument can then be used comfortably both by a right-handed surgeon and by a left-handed surgeon when taking hold of the instrument by means of one of its outer prongs.

Under such circumstances, the instrument is preferably constituted by two substantially U-shaped parts that are assembled together side by side by a mechanism enabling the spacing between the parts to be adjusted, the adjacent prongs of the U-shapes of the two parts together forming the inner pair of prongs, with the remoter prongs forming the handle. The design of the instrument turns out to be particularly simple and easy to make. Better still, the two U-shaped parts are symmetrical about an orthogonal plane, and the webs joining together the prongs of the U-shaped parts are arcuate. The even further simplified appearance of the instrument makes it easy to handle from one side or the other. The acruate junction between the parts facilitates insertion of the inner prongs into the sheath without the instrument rubbing against the heel of the foot.

Usefully, the mechanism for assembling the two parts together, side by side, comprises at least one rod attached to one of the parts and sliding in a hole formed correspondingly in the other part, together with a screw rotatably mounted in one of the parts and having its thread engaged in a tapped hole formed in the other part, the head of the screw being accessible externally for handling purposes. The adjustment mechanism is likewise simple to make and obvious to use.

Preferably, the eye of the needle is of reduced thickness. The reduction in the thickness of the eye takes account of the thickness of the thread, the eye and the thread being capable of passing through the orifices without any risk of the thread being sheared or cut.

Usefully, the instrument and the needle are made of stainless steel, or else the instrument is for single use only and is made of plastic.

The invention will be better understood on studying an embodiment taken by way of non-limiting example and illustrated in the following figures:

FIG. 1 shows apparatus for taking hold of an Achilles tendon, the apparatus comprising firstly an instrument 20 designed to be inserted in part inside the peritendinous sheath, and secondly a needle 10 designed to pass a thread through the raised top part of the tendon.

Figure 1:
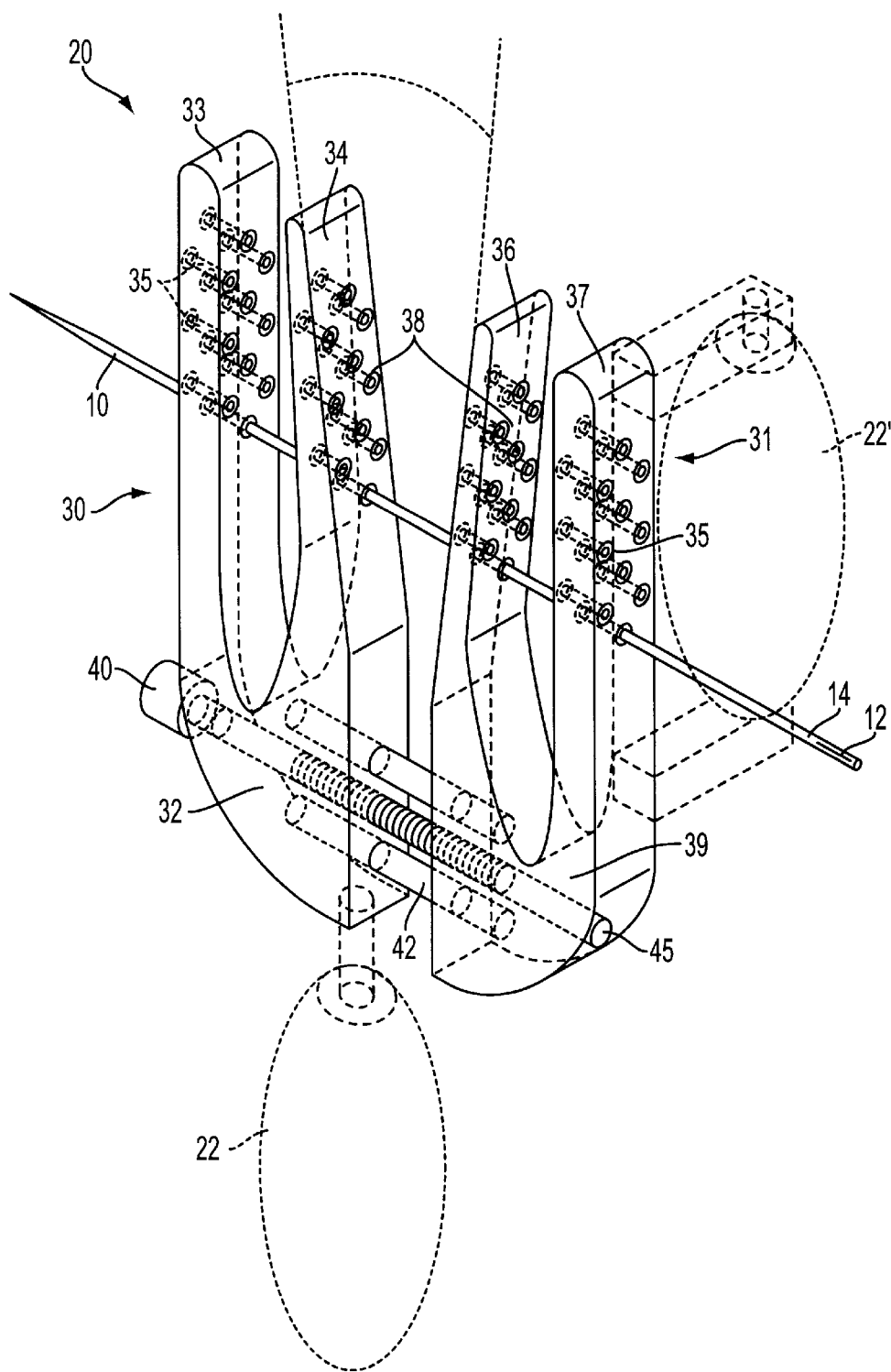
FIG. 1 is a perspective view of the apparatus of the invention.

As shown, the instrument 20 is in the form of two U-shaped pieces 30 and 31 that are assembled together by two holding pins 42 and that are held at a desired spacing by means of an adjustment screw 40. As can be seen, the two U-shaped parts 30 and 31 are completely symmetrical to each other about a midplane orthogonal to the needle 10.

Each U-shaped part thus has two prongs 33 & 34, 36 & 36 that are united by respective joining webs 32 and 39. The two outer prongs 33 and 37 are substantially rectilinear and quite thick, i.e. they are about 70 mm tall and have a constant cross-section that is about 7 mm wide and 12 mm deep. Conversely, the two inner prongs 34 and 36 which are of substantially the same height, are of finer section, and in particular they taper upwards. For example, near the bottom, the prongs 34 and 36 are of a section that is substantially rectangular being 5 mm wide and 12 mm deep, with said width reducing to about 2 mm near the top. It should be observed that the inner prongs 34 and 36 are not parallel to each other, unlike the outer prongs 33 and 37, but form between them an upwardly open angle lying in the range 2° to 8°, and preferably being 4°. The length of the prongs 34 and 36 corresponds to the maximum height to which it is observed that the tendon rises due to contraction of the muscle.

The webs 32 and 39 are of sufficient volume to contain the mechanism for connecting and adjusting the two U-shaped parts 30 and 31 relative to each other. More particularly, the mechanism comprises a pair of holding pins 42 attached to one of the parts, e.g. the part 30, and sliding in corresponding blind orifices formed in the web 39 of the other part 31. These two pins 42 thus hold the parts 30 and 31 in a first plane. The mechanism also comprises an adjustment screw 40 that is mounted to be free to rotate but that is held axially in one of the webs, e.g. in the web 32 of the part 30, with the threaded rod of the screw 30 being engaged in a tapped orifice 45 formed correspondingly in the other web 39. For reasons of balance, the adjustment screw is preferably installed halfway between the two pins 42.

As with any surgical instrument, all of the edges of the parts 30 and 31 are rounded to avoid catching or even cutting soft tissue. More particularly, the top ends of the inner prongs 34 and 36 are rounded using two successive circular curves, an inner first curve having a radius of about 5 mm and an outer end curve having a radius of about 1.7 mm.

In accordance with the invention, all of the prongs of the two parts have the same array of orifices 35, 38, with four orifices in respective ones of the prongs always being situated in line with one another so as to receive the needle 10, as shown in FIG. 1. The inside diameter of the orifices lies in the range 0.8 mm to 2 mm, and is preferably 1.6 mm. The orifices have inlet and outlet chamfers of diameter of about 2.5 mm. Given the width of about 7 mm of the outer prongs 33 and 37, the orifices 35 in these prongs act as guide orifices for needle 10 so that the needle is necessarily controlled so as to be capable of being inserted in the orifices 38 through the inner prongs 34, 36. The chamfers formed in the mouths of these orifices facilitate such insertion.

If so desired and in addition to the handle function of the outer prongs 33 and 37, the instrument 20 may also have larger handles which are thus easier to hold. For example, a first handle 22 can be disposed beneath the web 32 of the part 30, projecting from the bottom thereof. Alternatively, a handle 22' can be organized parallel to one of the outer prongs 33 or 37.

Like most instruments used in surgery, the instrument 20 of the invention can be made of polished stainless steel suitable for being sterilized after each operation. Alternatively, and for considerations of cost, it is also possible for the instrument 20 to be made of a sterile plastics material, with the instrument then being designed for single use only.

In association with the instrument 20, the apparatus comprises a needle 10 of diameter lying in the range 0.7 mm to 1.9 mm, and preferably equal to 1.5 mm, so that the needle is sufficiently rigid without being traumatizing. The length of the needle is preferably greater than the width of the instrument, i.e. about 80 mm, although it would also be possible to use needles that are longer or that are shorter. More particularly, the eye 12 of the needle is formed in a constriction 14 of smaller thickness so that together with the thread that forms a loop at this location, the total diameter of the needle remains smaller than the 1.6 mm diameter of the orifices 35 and 38 through which it is to pass.

By means of this apparatus, the operating technique for repairing the Achilles tendon is considerably facilitated as explained below. After the patient has been installed and then anesthetized, the surgeon makes a small incision that is about 2 cm to 3 cm long and that is advantageously vertical. The surgeon can then insert the inner prongs 34 and 36 through the incision into the peritendinous sheath and cause said prongs to move up inside the sheath until the distal end of the tendon is reached. Since the prongs 34 and 36 present an open angle, they naturally take up positions on either side of the tendon, and match its conical shape. The presence of the tendon between the prongs 34 and 36 can easily be observed by touch.

In this situation, it suffices to insert the needle 10 into one of the guide orifices 35 so that after passing through the skin, it necessarily passes through the corresponding orifice in the adjacent inner prong, e.g. 36, thus directing it into the tendon which, on being pierced, is held by the other inner prong 34, opposite. As the needle 10 continues to advance it penetrates into the through orifice of the prong 34 and leaves the skin, passing through the guide orifice 35 of the outer prong 33 opposite. Two other additional threads can then be put radially into place in the same manner. Once the desired number of threads have been put into place, the instrument 20 is pulled out slowly so that the inner prongs 34 and 36 are withdrawn from the sheath and take with them the threads that have passed through the tendon. These six thread ends then come out through the small incision that was made initially.

This operation of taking hold of the tendon is repeated on the other end of the tendon, specifically the end attached to the calcaneum. Twelve thread ends are then obtained making it possible to bring the ends of the tendon end to end for suturing. The threads are also knotted together, with the ends of a top loop being paired with the ends of a bottom loop.

As will have been seen on reading the above description, this simple apparatus greatly facilitates an operation that is difficult to perform.

Figure 2:
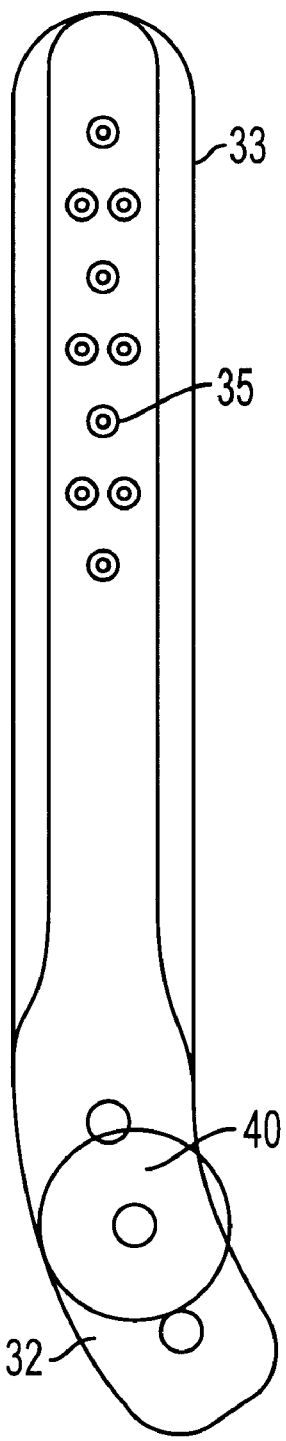
FIG. 2 is a side view of a variant of the instrument.

Numerous improvements can be provided to the instrument within the ambit of the invention. In particular, as can be seen more clearly in FIG. 2, the webs 32 and 39 can be curved so as to enable the prongs 34 and 36 to be inserted along the peritendinous sheath without running the risk of rubbing or colliding against the heel of the foot.

If so desired, one of the holding pins 42 can be omitted, making do with a single larger pin that operates in association with the adjustment screw. The holding pin need not be circular in section, but could be polygonal in section, being circular or rectangular, to prevent the U-shaped parts rotating relative to each other. It is also possible to envisage a device for locking the screw once the spacing has been adjusted, e.g. a lock nut organized between the two parts 30 and 31.

What is claimed is:

1. An apparatus for taking hold of a tendon in its peritendinous sheath, said apparatus comprising an instrument and a needle, wherein:

said instrument comprises:
a pair of inner prongs situated in a plane and configured to be insertable into the sheath; and
an external handle having at least one element situated in the plane and in register with said inner prongs, and further wherein:
said element and said inner prongs each have at least one orifice;
said at least one orifice in said element and said at least one orifice in each of said inner prongs are in alignment with one another along a line that passes through the tendon when said inner prongs are inserted into the peritendinous sheath; and
said needle is adapted to be inserted into said at least one orifice of said element and to be guided so as to pass through said at least one orifice of each of said inner prongs.

2. The apparatus according to claim 1 wherein said element and said inner prongs each have a set of orifices, and the orifices of each set are aligned with the orifices of each other set.

3. The apparatus according to claim 2 wherein each of said orifices has two ends which are chamfered.

4. The apparatus according to claim 1 wherein said pair of inner prongs form between them an angle in the range of 2° to 8°, the angle opening in the direction of insertion of said inner prongs into the peritendinous sheath.

5. The apparatus of claim 4, wherein the angle has a value of 4°.

6. The apparatus of claim 1 wherein each of said inner prongs is of rectangular cross-section that is flattened with rounded corners, or is of flattened oval section.

7. The apparatus of claim 6 wherein each of said inner prongs has a free end and is tapered toward said free end.

8. The apparatus of claim 1 wherein said inner prongs are spaced apart by an adjustable distance.

9. The apparatus of claim 1 wherein said at least one element comprises two elements in the form of outer prongs between which said pair of inner prongs is disposed, and said inner prongs and outer prongs lie in a common plane.

10. The apparatus of claim 9 wherein each of said outer prongs forms a respective U-shaped part with a respective inner prong, and said apparatus further comprises a mechanism operatively associated with said U-shaped parts for varying the spacing between said parts.

11. The apparatus of claim 10 wherein said U-shaped parts are symmetrical to one another with respect to a plane perpendicular to the common plane.

12. The apparatus of claim 11 wherein each said U-shaped part has a web which joins together said inner prong and said outer prong of said U-shaped part and which is arcuate.

13. The apparatus of claim 11 wherein said mechanism comprises:
at least one rod attached to one of said U-shaped parts and sliding in a hole formed correspondingly in the other one of said U-shaped parts; and a screw rotatably mounted in one of said U-shaped parts and having a thread engaged in a tapped hole formed in the other one of said U-shaped parts, the screw having a head which is accessible externally for handling purposes.

14. The apparatus of claim 1 wherein said needle has a section of reduced thickness in which an eye is provided.

15. The apparatus of claim 1 wherein said needle is made of stainless steel and said instrument is made of stainless steel or plastic.

* * * * *